United States Patent [19]

Wagner et al.

[11] 4,119,738

[45] Oct. 10, 1978

[54] SWEET MATERIAL

[75] Inventors: Hans Wagner, Constance; Alfred Maierhofer, Allensbach, both of Germany

[73] Assignee: Deutsche Gold- und Silber-Scheideanstalt vormals Roessler, Frankfurt, Germany

[21] Appl. No.: 687,321

[22] Filed: May 17, 1976

[30] Foreign Application Priority Data

May 16, 1975 [DE] Fed. Rep. of Germany ....... 2521816
Apr. 5, 1976 [DE] Fed. Rep. of Germany ....... 2614585
Apr. 15, 1976 [DE] Fed. Rep. of Germany ....... 2616731

[51] Int. Cl.$^2$ ............................................. A23L 1/236
[52] U.S. Cl. ................................... 426/548; 426/549; 426/554; 426/577; 426/590; 426/591; 426/593; 426/594; 426/597; 426/660; 562/579

[58] Field of Search ............... 426/548, 590, 591, 593, 426/594, 597, 804, 534, 285, 453, 549, 554, 577, 660; 260/535 R

[56] References Cited

U.S. PATENT DOCUMENTS 3,627,583  12/1971  Tray .................................. 426/285 X
3,853,996  12/1974  Begemann et al. .............. 426/534 X

OTHER PUBLICATIONS

Verbit et al., *Tetrahedron*, 24(3), (1968), pp. 1231–1236.
Chemical Abstracts 82: 144958, (1975).

*Primary Examiner*—Raymond N. Jones
*Assistant Examiner*—Esther M. Kepplinger
*Attorney, Agent, or Firm*—Cushman, Darby & Cushman

[57] ABSTRACT

2-Hydroxy-4-methyl valeric acid and its salts are useful as sweeteners. The preferred sweeteners are the sodium and potassium salts.

26 Claims, No Drawings

SWEET MATERIAL

The invention concerns sweeteners.

Numerous chemical compounds are known which taste sweet. However, only a few of them can be used as sweeteners by having a high sweetening value, no disturbing after taste, are stable under the conditions under which sweeteners are added and in long time use are considered physiologically unobjectionable.

As sweeteners there are used almost exclusively dulcin (p-phenetolcarbamide), saccharin, as well as sodium cyclamate and calcium cyclamate (Ullmanns Enzyklopadie der technischen Chemie, Urban and Schwarzenberg, Munich and Berlin Vol. 16 (1965) page 478). Of these compounds, dulcin has shown limited toxicity (Naturwissenschaften, Vol. 45 (1958) page 390). Therefore, it is not permitted as a sweetener in several countries or has only a limited sale. Saccharin and the cyclamates have shown carcinogenic activity in animals according to recent knowledge (Naturwissenschaften Vol. 61 (1974) page 22). Consequently their use as sweeteners is likewise objectionable.

It is also known to add 1-alanine-tert. butyl ester or 1-aspartyl-1-phenyl-alanine methyl ester as a sweetener (Naturwissenschaften Vol. 61 (1974) page 22; Chem. Eng. News Vol. 52 (1974) Issue 3 (page 5). These compounds, however, are difficultly accessible, besides have little heat stability and, therefore, are of only limited use.

It has now been found that 2-hydroxy-4-methyl valeric acid and especially the salts, i.e., the non-toxic salts of this acid are sweeteners. The acid and its salts have a sweetening value which exceeds that of sodium cyclamate or is its equal. Particularly the salts are free of aftertaste and are generally usable as sweeteners. Since they are thermally stable, they can be used for example as sweeteners of hot foods and baked goods. Besides, it is advantageous that the acid and its salts can be produced in a simple manner from easily accessible materials. Aqueous solutions, for example, of the sodium salt have been tested as nutrient solutions and are considered unobjectionable physiologically.

As sweeteners, there can be used 2-hydroxy-4-methyl valeric acid and its physiologically compatible salts, namely, both in the D,L-form and also in the D-form and the L-form. Suitable salts are chiefly the salts of the alkali metals such as lithium, sodium and potassium, the salts of the alkaline earth metals such as magnesium and calcium, the aluminum salt and the ammonium salt. The preferred sweeteners are the potassium and sodium salts of D,L-2-hydroxy-4-methyl valeric acid, with the sodium salt being most preferred.

The sweetening values of salts of 2-hydroxy-4-methyl valeric acid are compared with the sweetening values of known sweeteners in the following table (sweetening value determined according to Naturwissenschaften Vol. 61 (1974) page 22; Ann. Eugen. Vol. 15 (1949), page 24):

| Sweetener | Threshold Value (millimoles/liter) |
| --- | --- |
| Sucrose | 10.4 |
| Sodium cylamate | 0.28 |
| Potassium salt of D,L-2-hydroxy-4-methyl valeric acid | 0.27 |
| Sodium salt of D,L-2-hydroxy-4-methyl valerica cid | 0.24 |
| Saccharin | 0.015 |

The high sweetening value of 2-hydroxy-4-methyl valeric acid and its salts is very surprising since the salts of 2-hydroxy carboxylic acids as for example 2-hydroxy isovaleric acid, 2-hydroxy-3-methyl valeric acid, 2-hydroxypropionic acid and 2-hydroxy-4-methylmercaptobutyric acid do not taste sweet.

The 2-hydroxy-4-methyl valeric acid or its salts used as sweeteners can be added directly as such as sweeteners for food and drinks. In a given case, they can also be used in admixture with other materials either as solids or liquids.

Thus, the 2-hydroxy-4-methyl valeric acid or its salts, e.g., the sodium salt can be prepared in the form of a tablet, e.g., a tablet containing the sweetener in an amount having the same sweetening power as 1 to 2 teaspoons of sugar. Examples of tablets are a tablet containing 200 mg of the sodium salt of D,L-2-hydroxy-4-methylvaleric acid or a tablet containing 400 mg of the sodium salt or a tablet containing 200 mg of the potassium salt of D,L-2-hydroxy-4-methyl valeric acid or a tablet containing 90 mg of the sodium salt of D,L-2-hydroxy-4-methyl valeric acid and 3.2 mg of sodium saccharin. Such tablets, for example, can be added to coffee, tea or chocolate dissolved in water or milk for example.

The sweeteners of the invention can also be added to either carbonated (pressure) or non carbonated flavored beverages such as ginger ale, cream soda, grape soda, orange soda, root beer, chocolate water, cola drinks, coffee, tea or the like. Thus, the sugar in a 1 liter bottle of ginger ale can be replaced by 0.24 millimoles of the sodium salt of D,L-2-hydroxy-4-methyl valeric acid.

The sweeteners can also be added to solid foods, such as candy, cake mixes, jelly or jam. The sweeteners are added to the foodstuff in an amount sufficient to be effective as a sweetener.

The sweetening material of the invention can also be used in baked goods for diabetics. For example, there can be employed a baking composition composed of 250 grams of wheat meal, 250 grams of fat and 5 eggs to which there is added 6 grams of the sodium salt of D,L-2-hydroxy-4-methyl valeric acid. With the addition of sweetener, the baked goods are as sweet as with the addition of 250 grams of sucrose.

The 2-hydroxy-4-methyl valeric acid can be prepared for example by a conventional process for the production of a 2-hydroxy carboxylic acid by reaction of isovaleraldehyde with hydrogen cyanide and hydrolysis of the cyanhydrin formed with an acid (Organic Synthesis, Collected Vol. I (1941), page 336. The salts of the 2-hydroxy-4-methyl valeric acid can be obtained for example by neutralizing an aqueous solution of the acid with the corresponding metal hydroxide, e.g., sodium hydroxide, potassium hydroxide or calcium hydroxide, and the mixture evaporated or spray dried. The thus recovered salt has the necessary purity for use as a sweetener.

What is claimed is:

1. A foodstuff containing a compound selected from the group consisting of the sodium and potassium salts of 2-hydroxy-4-methyl-valeric acid in an amount effective to act as a sweetener therefor, said foodstuff being selected from the group consisting of flavored beverages, baked goods, candy, cake mixes, jelly and jam.

2. A foodstuff according to claim 1 which is a flavored beverage.

3. A beverage according to claim 2 which is a carbonated beverage.

4. A beverage according to claim 2 wherein the beverage is coffee, tea or chocolate.

5. A flavored beverage according to claim 2 wherein the compound is the sodium salt of D,L-2-hydroxy-4-methyl valeric acid.

6. A flavored beverage according to claim 2 wherein the compound is the potassium salt of D,L-2-hydroxy-4-methyl valeric acid.

7. A solid foodstuff according to claim 1.

8. A solid foodstuff according to claim 7 wherein the compound is the sodium salt of D,L-2-hydroxy-4-methyl valeric acid.

9. A solid foodstuff according to claim 7 wherein the compound is the potassium salt of D,L-2-hydroxy-4-methyl valeric acid.

10. A foodstuff according to claim 1 wherein the compound is the sodium salt of D,L-2-hydroxy-4-methyl-valeric acid.

11. A foodstuff according to claim 1 wherein the compound is the potassium salt of D,L-2-hydroxy-4-methyl-valeric acid.

12. A foodstuff according to claim 1 which is a flavored beverage, said compound is the sodium salt or the potassium salt and said compound is present in an amount of at least 0.24 millimoles/liter when it is the sodium salt and in an amount of at least 0.27 millimoles/liter when it is the potassium salt.

13. A foodstuff according to claim 1 which is a baking composition composed of 250 grams wheat meal, 250 grams of fat, 5 eggs and 6 grams of the sodium salt of D,L-2-hydroxy-4-methyl-valeric acid.

14. A process of sweetening a foodstuff selected from the group consisting of flavored beverages, baked goods, candy, cake mixes, jelly and jam comprising adding to the foodstuff the sodium or potassium salt of 2-hydroxy-4-methyl-valeric acid in an amount effective to act as a sweetener therefor.

15. A process according to claim 14 wherein the compound is the sodium salt.

16. A process according to claim 14 wherein the foodstuff is a cake mix, jelly or jam.

17. A process according to claim 14 wherein the foodstuff is a flavored beverage.

18. A process according to claim 15 wherein the foodstuff is a flavored beverage and there is added at least 0.27 millimoles/liter of the potassium salt of D,L-2-hydroxy-4-methyl-valeric acid or at least 0.24 millimoles/liter of the sodium salt of D,L-2-hydroxy-4-methyl-valeric acid.

19. A tablet suitable for sweetening food comprising the sodium or potassium salt of 2-hydroxy-4-methyl-valeric acid.

20. A tablet according to claim 19 which consists essentially of said sodium or potassium salt.

21. A tablet according to claim 20 wherein the salt is the sodium salt.

22. A tablet according to claim 21 wherein the salt is the sodium salt and the tablet contains 200 to 400 mg of said salt.

23. A tablet according to claim 19 consisting essentially of said sodium or potassium salt and saccharin.

24. A tablet according to claim 20 wherein when the salt is the sodium salt the tablet contains 200 to 400 mg of the salt and when the salt is the potassium salt the tablet contains 200 mg of the salt.

25. A tablet according to claim 24 wherein the compound is the potassium salt of D,L-2-hydroxy-4-methyl valeric acid.

26. A tablet according to claim 20 containing an amount of said compound having the sweetening power of 1 to 2 teaspoons of sugar.

* * * * *